United States Patent [19]

Lang et al.

[11] Patent Number: 5,373,024
[45] Date of Patent: Dec. 13, 1994

[54] 3,5-SUBSTITUTED BENZOYLGUANIDINES, PROCESS FOR THEIR PREPARATION, THEIR USE AS A MEDICAMENT OF DIAGNOSTIC AND MEDICAMENT CONTAINING THEM

[75] Inventors: Florian Lang, Markdorf; Hans-Jochen Lang, Hofheim am Taunus; Dieter Mania, Königstein/Taunus; Andreas Weichert, Frankfurt am Main; Wolfgang Scholz, Eschborn; Udo Albus, Florstadt; Heinrich Englert, Hofheim am Taunus, all of Germany

[73] Assignee: Hoechst Aktiengesellschaft, Frankfurt am Main, Germany

[21] Appl. No.: 15,926

[22] Filed: Feb. 10, 1993

[30] Foreign Application Priority Data

Feb. 15, 1992 [DE] Germany ............... 4204575

[51] Int. Cl.$^5$ .............. C07C 279/22; A61K 31/18; A61K 31/155
[52] U.S. Cl. .............. 514/618; 514/522; 514/603; 514/634; 514/821; 558/413; 564/86; 564/162; 564/237
[58] Field of Search ............. 564/162, 237, 86; 514/618, 634, 821, 603, 522; 558/413

[56] References Cited

U.S. PATENT DOCUMENTS 3,780,027 12/1973 Cragoe, Jr. et al. ............ 260/239.6
5,091,394 2/1992 Englert et al. .................... 514/331

FOREIGN PATENT DOCUMENTS

0416499A3 3/1991 European Pat. Off. .

OTHER PUBLICATIONS

Duff et al., "Amiloride", *Circulation*, vol. 79, No. 6, Jun. 1989 pp. 1257-1263.
Eur. Heart of J.9 (suppl. 1):25 and 167 (1988) book of abstracts.
A. Schmid et al., "Na+/H+ Exchange in Porcine Cerebral Capillary Endothelial Cells is Inhibited by a Benzoylguanidine Derivative," Biochemical and Biophysical Research Communications, Apr. 15, 1992, pp. 112-117.

*Primary Examiner*—Peter O'Sullivan
*Attorney, Agent, or Firm*—Finnegan, Henderson, Farabow, Garrett & Dunner

[57] ABSTRACT

Benzoylguanidines of the formula I

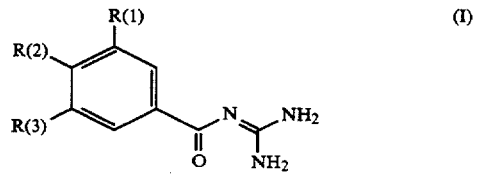

are described where R(1) is R(4)—SO$_m$ or R(5)R(6)N—SO$_z$—, where R(4) and R(5) are alk(en)yl or —C$_n$H$_{2n}$—R(7), and where R(7) is a cycloalkyl or phenyl, where R(5) also has the meaning of H, and R(6) is H or C$_1$-C$_4$-alkyl, R(2) is hydrogen, halogen, alkyl, O—(CH$_2$)$_m$C$_p$F$_{2p+1}$, —X—R(10), where X is O, S or NR(11), R(10) is H, (cyclo)alkyl(methyl) or —C$_n$H$_{2n}$—R(12) where R(12) is phenyl, and R(3) is defined, inter alia, as R(1), and their pharmaceutically tolerable salts.

The compounds I are obtained by reaction of compounds of the formula II

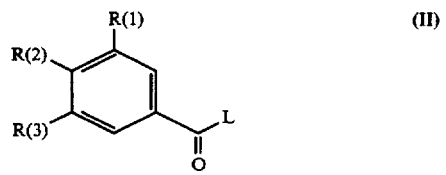

with guanidine, in which L is a leaving group which can be easily nucleophilically substituted.

Compounds I are outstandingly suitable as antiarrythmic pharmaceuticals having a cardioprotective component for infarct prophylaxis and infarct treatment and for the treatment of angina pectoris, where they also (Abstract continued on next page.)

preventively inhibit or greatly reduce the pathophysiological processes during the formation of ischemically induced damage. They are moreover distinguished by strong inhibitory action on the proliferation of cells. They can therefore be used as antiatherosclerotics, agents against late-onset diabetic complications, cancers, and fibrotic diseases such as pulmonary fibrosis, fibrosis of the liver or fibrosis of the kidneys.

They are effective inhibitors of the cellular sodium/proton antiporter ($Na^+/H^+$ exchanger).

7 Claims, No Drawings

3,5-SUBSTITUTED BENZOYLGUANIDINES, PROCESS FOR THEIR PREPARATION, THEIR USE AS A MEDICAMENT OF DIAGNOSTIC AND MEDICAMENT CONTAINING THEM

The invention relates to benzoylguanidines of the formula I
in which:

$R(1)$ is $R(4)$—$SO_m$ or $R(5)R(6)N$—$SO_2$—, where
  m is zero, 1 or 2,
  $R(4)$ and $R(5)$ are $C_1$-$C_6$-alkyl, $C_3$-$C_6$-alkenyl or —$C_nH_{2n}$—$R(7)$,
    n is zero, 1, 2, 3 or 4,
    $R(7)$ is $C_5$-$C_7$-cycloalkyl or phenyl which is unsubstituted or substituted by 1-3 substituents from the group comprising
      F, Cl, $CF_3$, methyl, methoxy and $NR(8)R(9)$
        where $R(8)$ and $R(9)$ are H or $C_1$-$C_4$-alkyl,
  where $R(5)$ also has the meaning of H, $R(6)$ is H or $C_1$-$C_4$-alkyl,
  where $R(5)$ and $R(6)$ together can be 4 or 5 methylene groups, of which one $CH_2$ group can be replaced by O, S, NH, N—$CH_3$ or N-benzyl,
$R(2)$ is hydrogen, F, Cl, Br, ($C_1$-$C_4$)-alkyl, O—$(CH_2)_mC_pF_{2p+1}$ or —X—$R(10)$, where
  m is zero or 1,
  p is 1, 2 or 3,
  x is O, S, or $NR(11)$,
  $R(10)$ is H, $C_1$-$C_6$-alkyl, $C_5$-$C_7$-cycloalkyl, cyclohexylmethyl, cyclopentylmethyl, or —$C_nH_{2n}$—$R(12)$ where
    n is zero, 1, 2, 3 or 4 and
    $R(12)$ is phenyl which is unsubstituted or substituted by 1-3 substituents from the group comprising
      F, Cl, $CF_3$, methyl, methoxy and $NR(8)R(9)$
        where $R(8)$ and $R(9)$ are H or $C_1$-$C_4$-alkyl
  $R(11)$ is H or $C_1$-$C_3$-alkyl
    where $R(10)$ and $R(11)$ can also together be 4 or 5 methylene groups and a $CH_2$ group can be replaced by O, S, NH, N—$CH_3$ or N-benzyl,
$R(3)$ is defined as $R(1)$, or is $C_1$-$C_6$-alkyl, nitro, cyano, trifluoromethyl, F, Cl, Br, I or —X—$R(10)$ where
  X is O, S or $NR(11)$,
  $R(10)$ is H, $C_1$-$C_6$-alkyl, $C_5$-$C_7$-cycloalkyl, cyclohexylmethyl, cyclopentylmethyl or —$C_nH_{2n}$—$R(12)$ where
    n is from zero to 4 and
    $R(12)$ is phenyl which is unsubstituted or substituted by 1-3 substituents from the group comprising
      F, Cl, $CF_3$, methyl, methoxy and $NR(8)R(9)$
        where $R(8)$ and $R(9)$ are H or $C_1$-$C_4$-alkyl,
  $R(11)$ is H or $C_1$-$C_3$-alkyl,
    where $R(10)$ and $R(11)$ can also together be 4 or 5 methylene groups and a $CH_2$ group can be replaced by O, S, NH, N—$CH_3$ or N-benzyl,
and their pharmaceutically tolerable salts,
but where compounds are excluded in which, at the same time:
  $R(1)$ is $R(4)$—$SO_m$ where m=zero to 2 or $R(5)R(6)NSO_2$—,
  $R(2)$ is halogen, ($C_1$-$C_4$)-alkyl, and
  $R(3)$ is —$NR(10)R(11)$.

Preferred compounds of the formula I are those in which:

$R(1)$ is $R(4)$—$SO_m$ or $R(5)R(6)N$—$SO_2$—,
  m is zero, 1 or 2,
  $R(4)$ is methyl or —$C_nH_{2n}$—$R(7)$,
    n is zero or 1,
    $R(7)$ is phenyl which is unsubstituted or substituted by 1-3 substituents from the group comprising Cl, $CF_3$, methyl and methoxy,
  $R(5)$ is H, $C_1$-$C_6$-alkyl, allyl or —$C_nH_{2n}$—$R(7)$,
    n is zero or 1, 2 or 3
    $R(7)$ is phenyl which is unsubstituted or substituted by 1-3 substituents from the group comprising
      F, Cl, $CF_3$, methyl and methoxy and $NR(8)R(9)$ where $R(8)$ and $R(9)$ are H or methyl,
  $R(6)$ is H or methyl, where $R(5)$ and $R(6)$ can together be 4 or 5 methylene groups, of which one $CH_2$ group can be replaced by an O, S, N—$CH_3$ or N-benzyl,
$R(2)$ is hydrogen, O—$CH_2CF_3$ or —X—$R(10)$, where
  X is O, S or $NR(11)$,
  $R(10)$ is H, $C_1$-$C_6$-alkyl or —$C_nH_{2n}$—$R(12)$ where
    n for X having the meaning of oxygen or sulfur is zero, and for X having the meaning of $NR(12)$ is zero or 1, and $R(12)$ is phenyl which is unsubstituted or substituted by 1-3 substituents from the group comprising
      F, Cl, $CF_3$ and methyl,
  $R(11)$ is H or ($C_1$-$C_3$)-alkyl,
    where $R(10)$ and $R(11)$ can also together be 4 or 5 methylene groups and a $CH_2$ group can be replaced by O, S, N—$CH_3$ or N-benzyl,
$R(3)$ is methyl, nitro, cyano, trifluoromethyl, F, Cl or —X—$R(10)$ where
  X is O, S or $NR(11)$,
  $R(10)$ is H, $C_1$-$C_6$-alkyl or —$C_n$—$H_{2n}$—$R(12)$ where
    n is zero or 1,
    $R(12)$ is phenyl which is unsubstituted or substituted by 1-3 substituents from the group comprising Cl, $CF_3$, methyl and methoxy,
  $R(11)$ is H or ($C_1$-$C_3$)-alkyl
    where $R(10)$ and $R(11)$ can also together be 4 or 5 methylene groups,
and their pharmaceutically tolerable salts.

Particularly preferred compounds of the formula I are those in which:

$R(1)$ is $R(4)$—$SO_2$— or $R(5)R(6)N$—$SO_2$— where
  $R(4)$ is methyl,
  $R(5)$ and $R(6)$ are hydrogen,
$R(2)$ is hydrogen, —O—$CH_2$—$CF_3$ or X—$R(10)$ where
  X is oxygen or N—$R(11)$,
  $R(10)$ is H, $C_1$-$C_6$-alkyl or —$C_nH_{2n}$—$R(12)$ where
    n=zero or 1
    $R(12)$ is phenyl which is unsubstituted or substituted by a substituent from the group comprising F, Cl and methyl,
  $R(11)$ is H or $C_1$-$C_3$-alkyl,
$R(3)$ is methyl, F or Cl, and their pharmacologically tolerable salts.

Very particularly preferred compounds are 3-chloro-4-N, N-diethylamino-5-methylsulfonylbenzoylguanidine hydrochloride and 3,4-dimethyl-5-sulfaraoylbenzoylguanidine hydrochloride.

If one of the substituents $R(1)$ to $R(12)$ contains a center of asymmetry, the invention includes compounds having both the S and R configuration. The compounds can be present as optical isomers, as diastereomers, as racemates or as mixtures thereof.

The designated alkyl radicals can be present either in straight-chain or branched form.

The invention furthermore relates to a process for the preparation of the compounds I, which comprises reacting compounds of the formula II
with guanidine, in which R(1) to R(3) have the given meaning and L is a leaving group which can be easily nucleophilically substituted.

The activated acid derivatives of the formula II in which L is an alkoxy group, preferably a methoxy group, a phenoxy group, or phenylthio, methylthio or 2-pyridylthio group, or a nitrogen heterocycle, preferably 1-imidazolyl, are advantageously obtained in a manner known per se from the carbonyl chlorides (formula II, L=Cl) on which they are based, which for their part can in turn be prepared in a manner known per se from the carboxylic acids (formula II, L=OH) on which they are based, for example using thionyl chloride.

In addition to the carbonyl chlorides of the formula II (L=Cl), other activated acid derivatives of the formula II can also be prepared in a manner known per se directly from the benzoic acid derivatives (formula II, L=OH) on which they are based, such as, for example, the methyl esters of the formula II where L=OCH$_3$ by treatment with gaseous HCl in methanol, the imidazolides of the formula II by treatment with carbonyldiimidazole (L=1-imidazolyl, Staab, Angew. Chem. Int. Ed. Engl. 1, 351–367 (1962)), the mixed anhydrides II using Cl—COOC$_2$H$_5$ or tosyl chloride in the presence of triethylamine in an inert solvent, and also the activation of benzoic acids using dicyclohexylcarbodiimide (DCC) or using O-[(cyano-(ethoxycarbonyl)methylene)amino]-1,1,3,3-tetramethyluronium tetrafluoborate ("TOTU") (Weiss and Krommer, Chemiker Zeitung 98, 817 (1974)). A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula I with guanidine is carried out in a manner known per se in a protic or aprotic polar but inert organic solvent. Methanol or THF between 20° C. and the boiling point of these solvents have proven suitable in the reaction of the methyl benzoates (II, L=OMe) with guanidine between 20° C. and the boiling point of these solvents. In most reactions of compounds II with salt-free guanidine, the reaction was advantageously carried out in aprotic inert solvents such as THF, dimethoxyethane or dioxane. However, water can also be used as a solvent in the reaction of II and III if a base such as, for example, NaOH is used.

If L=Cl, the reaction is advantageously carried out with the addition of an acid scavenger, for example in the form of excess guanidine for binding the hydrohalic acid.

Some of the underlying benzoic acid derivatives of the formula II are known and described in the literature. The unknown compounds of the formula II can be prepared by methods known from the literature.

Carboxylic acids or their esters of the formula II (for example L=—OH or —O-methyl) where R(2) has the meaning of halogen or R(3) has the meaning of nitro can be used as versatile starting compounds for other carboxylic acids of the formula II, it being possible to replace the halogen in the position R(2) very conveniently in a known manner by numerous nucleophilic reagents, such as mercaptans R(10)—SH, phenols R(10)—OH or primary or secondary amines R(10)R(11)NH with the formation of other benzoic acid derivatives II where L=—OH or —O-methyl or it being possible to convert nitro, after reductive transformation to NH$_2$, into other benzoic acid derivatives II where L=—OH or —O-methyl in numerous reactions (alkylations, acylations or diazotizations followed by Sandmeyer, Ullmann, Meerwein etc. reactions).

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates and p-toluene-sulfonates.

The compounds I are substituted acylguanidines.

A prominent ester representative of the acylguanidines is the pyrazine derivative amiloride, which is used in therapy as a potassium-sparing diuretic. Numerous other compounds of the aniloride type are described in the literature, such as, for example, dimethylamiloride or ethylisopropylamiloride.

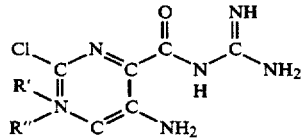

Amiloride: R', R''=H
Dimethylamiloride: R', R''=CH$_3$
Ethylisopropylamiloride: R'=C$_2$H$_5$, R''=CH(CH$_3$)$_2$ Investigations have moreover been disclosed which point to antiarrhythmic properties of amiloride (Circulation 79, 1257–63 (1989)). Obstacles to wide use as an antiarrhythmic are, however, that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts (Eur. Heart J. 9 (suppl.1): 167 (1988) (book of abstracts)). For instance, it was found in rat hearts that an artificially induced ventricular fibrillation could be suppressed completely by amiloride. The above-mentioned amiloride derivative ethylisopropylamiloride was even more potent than amiloride in this model.

U.S. Pat. No. 5,091,394 (HOE 89/F 288) describes benzoylguanidines which carry a hydrogen atom in the position corresponding to the radical R(1).

In U.S. Pat. No. 3,780,027, acylguanidines are claimed which are structurally similar to the compounds of the formula I and are derived from commercially available loop diuretics, such as bumetanide. A strong salidiuretic activity is correspondingly reported for these compounds.

It was therefore surprising that the compounds according to the invention have no undesired and disadvantageous salidiuretic properties, but very good antiarrhythmic properties, as occur, for example, in the case of oxygen deficiency symptoms. As a result of their pharmacological properties, the compounds are outstandingly suitable as antiarrhythmic pharmaceuticals having a cardioprotective component for infarct prophylaxis and infarct treatment and for the treatment of angina pectoris, where they also preventively prohibit or greatly decrease the pathophysiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular $Na^+/H^+$ exchange mechanism as pharmaceuticals for the treatment of all acute or chronic damage caused by ischemia or primary or secondary diseases induced thereby. This relates to their use as pharmaceuticals for surgical interventions, for example in organ transplantation, where the compounds can be used both for the protection of the organs in the donor before and during removal, for the protection of removed organs, for example during treatment with or storage thereof in physiological bath fluids, and during transfer to the body of the recipient. The compounds are also useful protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the central nervous system, where they are suitable, for example, for the treatment of stroke or of cerebral edema. Moreover, the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as antiatherosclerotics, agents against late-onset diabetic complications, cancers, fibrotic diseases such as pulmonary fibrosis, fibrosis of the liver or fibrosis of the kidneys, organ hypertrophy and hyperplasia, in particular in prostate hyperplasia or prostate hypertrophy.

The compounds according to the invention are active inhibitors of the cellular sodium-proton antiporter ($Na^+/H^+$ exchanger), which is raised in numerous diseases (essential hypertension, atherosclerosis, diabetes, etc.) even in those cells which are easily accessible to measurements, such as, for example, in erythrocytes, thrombocytes or leucocytes. The compounds according to the invention are therefore suitable as excellent and simple scientific tools, for example in their use as diagnostics for the determination and differentiation of certain forms of hypertension, but also of atherosclerosis or of diabetes, proliferative diseases etc. Moreover, the compounds of the formula I are suitable for preventive therapy for the prevention of the formation of high blood pressure, for example of essential hypertension.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise in veterinary and in human medicine.

The auxiliaries which are suitable for the desired pharmaceutical formulation are familiar to the person skilled in the art on the basis of his knowledge. In addition to solvents, gelling agents, suppository bases, tabletting auxiliaries and other active compound excipients, antioxidants, dispersants, emulsifiers, anti-foams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular corn starch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of these solvents.

If required, the formulation can also contain still other pharmaceutical auxiliaries such as surfactants, emulsifiers and stabilizers as well as a propellant gas. Such a preparation contains the active compound customarily in a concentration from about 0.1 to 10, in particular from about 0.3 to 3% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated.

On average, the daily dose of a compound of the formula I in a patient of weight about 75 kg is at least 0.001 mg/kg, preferably 0.01 mg to 10 mg/kg, preferably 1 mg/kg of body weight. In acute episodes of the disease, for example immediately after suffering a cardiac infarct, even higher and in particular more frequent dosages may be necessary, for example up to 4 individual doses per day. In particular when administered i.v., for example in the case of an infarct patient in the intensive care ward, up to 200 mg per day may be necessary.

Experimental Section

General procedure for the preparation of benzoylguanidines (I) from benzoic acids (II, L=OH) 0.01 Mol of the benzoic acid derivative of the formula II is dissolved or suspended in 60 ml of anhydrous tetrahydrofuran (THF) and then treated with 1.78 g (0.011 mol) of carbonyldiimidazole. After stirring for 2 hours at room temperature, 2.95 g (0.05 mol) of guanidine are introduced into the reaction solution. After stirring overnight, the THF is distilled off under reduced pressure (Rotavapor), the residue is treated with water, the mixture is adjusted to pH 6–7 with 2N HCl and the corresponding benzoylguanidine (formula I) is filtered off. The benzoylguanidines thus obtained can be converted into the corresponding salts by treatment with aqueous or methanolic hydrochloric acid or other pharmacologically tolerable acids.

EXAMPLE 1

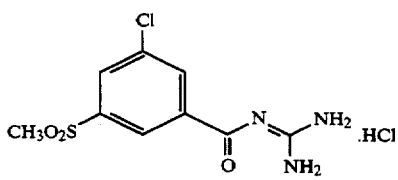

3-Chloro-5-methylsulfonylbenzoylguanidine hydrochloride: Colorless crystals, melting point 230° C. Synthesis route:
- a) Reduction of 3-chloro-5-chlorosulfonylbenzoic acid to 3-chloro-5-carboxybenzenesulfinic acid using sodium bisulfite in water at 10°–15° C. and a constant pH of 8–9 (NaOH, glass electrode), acidify with HCl and filter off the white precipitate.
- b) Disodium 3-chloro-5-carboxybenzenesulfinate from a) using 2 equivalents of NaOH in water, evaporate, suspend in acetone and filter off crystals; white crystals, melting point >300° C.
- c) Methyl 3-chloro-5-methylsulfonylbenzoate from b) using 1 equivalent of methyl iodide in DMF at 80° C./8 hours, distill off solvent, column chromatography on silica gel and ethyl acetate/toluene mixture (1:3). Colorless crystals, melting point 75° C.
- d) 3-Chloro-5-methylsulfonylbenzoic acid from c) by alkaline hydrolysis and acidification with HCl. White crystalline powder, melting point 214° C.
- e) 3-Chloro-5-methylsulfonylbenzoylguanidine hydrochloride from d) according to the general procedure (see above). Colorless crystals, melting point 230° C.

EXAMPLE 2

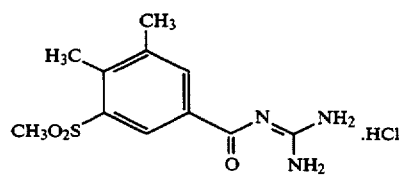

3,4-Dimethyl-5-methylsulfonylbenzoylguanidine hydrochloride; colorless crystals, melting point 288° C. Synthesis route:
- a) 2,3-Dimethyl-5-carboxybenzenesulfinic acid from 5-chlorosulfonyl-3,4-dimethylbenzoylbenzoic acid by reduction with sodium bisulfite analogously to Example 1, a), white crystals, melting point 213° C.
- b) Disodium2,3-dimethyl-5-carboxybenzenesulfinate from 2,3-dimethyl-5-carboxybenzenesulfinic acid analogously to Example 1, b). Colorless crystals, melting point >320° C.
- c) Methyl 3,4-dimethyl-5-methylsulfonylbenzoate from disodium 2,3-dimethyl-5-carboxybenzenesulfinate analogously to Example 1, c). Colorless crystals, melting point 102° C.
- d) 3,4-Dimethyl-5-methylsulfonylbenzoic acid from methyl 13,4-dimethyl-5-methylsulfonylbenzoate analogously to Example 1, d). Colorless crystals from ethanol, melting point 224° C.
- e) 3,4-Dimethyl-5-methylsulfonylbenzoylguanidine hydrochloride according to the general procedure from 3,4-dimethyl-5-methylsulfonylbenzoic acid. Colorless crystals, melting point 288° C.

EXAMPLE 3

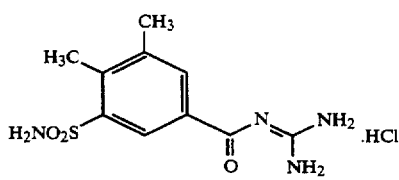

3,4-Dimethyl-5-sulfamoylbenzoylguanidine hydrochloride according to the general procedure from 3,4-dimethyl-5sulfamoylbenzoic acid. Colorless crystals, melting point 270° C.

EXAMPLE 4

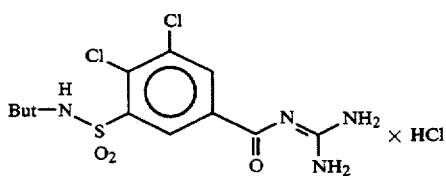

5-(1-Butylsulfamoyl)-3,4-dichlorobenzoylguanidine hydrochloride is obtained by reaction of 3,4-dichlorobenzoic acid in chlorosulfonic acid at 140°–160° C. with the production of 3,4-dichloro-5-chlorosulfonylbenzoic acid (melting point 203° C.), reaction with N-butylamine to give 5-(1-butylsulfamoyl)-3,4-dichlorobenzoic acid (melting point 160°–165° C.) and subsequent activation thereof with carbonyldiimidazole, reaction with guanidine and treatment with HCl to give 5-(1-butylsulfamoyl)-3,4-dichlorobenzoylguanidine hydrochloride, melting point 140°–145° C.

EXAMPLE 5

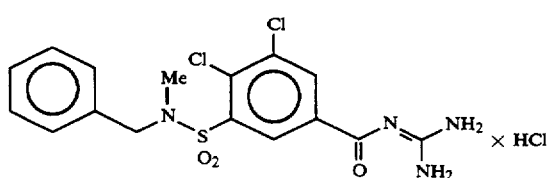

5-N-Benzyl-N-methylsulfamoyl-3,4-dichlorobenzoylguanidine hydrochloride is obtained by reaction of 3,4-dichloro-5-chlorosulfonylbenzoic acid with N-methylbenzylamine to give 5-N-benzyl-N-methylsulfamoyl-3,4-dichlorobenzamide, (melting point 155°–160° C.) and subsequent reaction according to the general procedure (see above):

5-N-benzyl-N-methylsulfamoyl-3,4-dichlorobenzoylguanidine hydrochloride. Colorless crystals, melting point 185°–190° C.

EXAMPLE 6

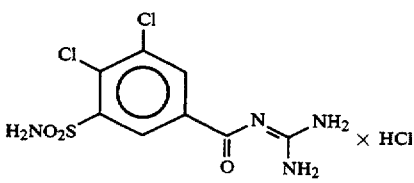

3,4-Dichloro-5-sulfamoylbenzoylguanidine hydrochloride (Colorless crystalline substance, melting point 234°–36° C.) is obtained from 3,4-dichloro-5-sulfamoylbenzoic acid according to the general procedure (see above).

EXAMPLE 7

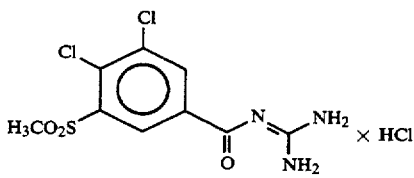

3,4-Dichloro-5-methylsulfonylbenzoylguanidine hydrochloride, colorless crystals, melting point 236°–240° C., is obtained starting from 3,4-dichloro-5-chlorosulfonylbenzoic acid by sulfite reduction to disodium 2,3-dichloro-5-carboxybenzenesulfinate (melting point >300° C.), reaction with excess methyl iodide to give methyl 3,4-dichloro-5methylsulfonylbenzoate, hydrolysis to 3,4-dichloro-5methylsulfonylbenzoic acid (196°–199° C.) and subsequent reaction according to the general procedure.

EXAMPLE 8

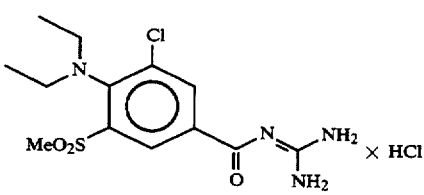

3-Chloro-4-N,N-diethylamino-5-methylsulfonylbenzoylguanidine hydrochloride, colorless crystals, melting point: 222°–224° C. is obtained starting from methyl 3,4-dichloro-5-methylsulfonylbenzoate by reaction with diethylamine in an autoclave (160° C., 12 hours) and subsequent alkaline hydrolysis to 3-chloro-4-N,N-diethylamino-5-methylsulfonylbenzoic acid (melting point 115°–117° C.) and reaction with guanidine according to the procedure (see above).

EXAMPLE 9

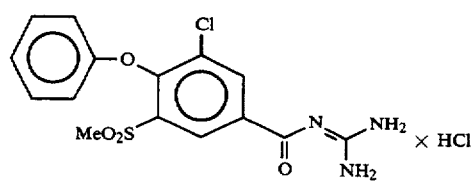

3-Chloro-5-methylsulfonyl-4-phenoxybenzoylguanidine hydrochloride, colorless crystals, melting point 271°–274° C., is obtained starting from methyl 3,4-dichloro-5-methylsulfonylbenzoate by reaction with phenol and potassium carbonate in DMF (80° C., 6.5 hours) and subsequent alkaline hydrolysis to 3-chloro-5-methylsulfonyl-4-phenoxybenzoic acid (melting point 210°–212° C.) and reaction with guanidine according to the procedure (see above).

EXAMPLE 10

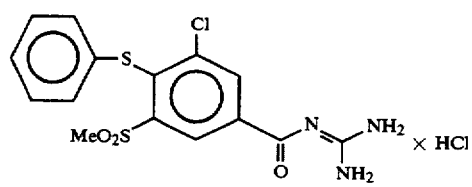

3-Chloro-5-methylsulfonyl-4-phenylthiobenzoylguanidine hydrochloride, colorless crystals, melting point 228°–230° C., is obtained starting from methyl 3,4-dichloro-5-methylsulfonylbenzoate by reaction with thiophenol and potassium carbonate in DMF (120° C., 6.5 hours) and subsequent alkaline hydrolysis to 3-chloro-5-methylsulfonyl-4-phenylthiobenzoic acid (melting point 231°–233° C.) and reaction with guanidine according to the procedure (see above).

EXAMPLE 11

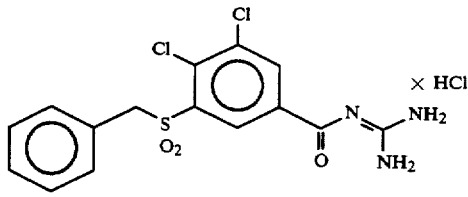

3-Benzylsulfonyl-4,5-dichlorobenzoylguanidine hydrochloride, colorless crystals, melting point: 262° C. is obtained by reaction of disodium 2,3-dichloro-5-carboxybenzenesulfonate with 2 equivalents of benzyl chloride in DMF (80° C., 5 hours) and subsequent acidic hydrolysis (20% strength aqueous HCl, in glacial acetic acid, 3 hours' reflux) to 5-benzylsulfonyl-3,4-dichlorobenzoic acid (melting point 183° C.) and subsequent reaction with guanidine according to the general procedure.

EXAMPLE 12

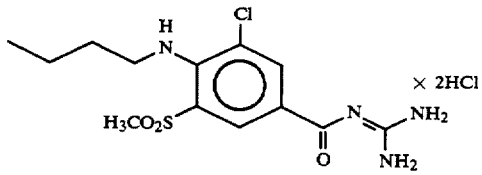

4-(1-Butylamino)-3-chloro-5-methylsulfonylbenzoylguanidine dihydrochloride, colorless crystals, melting point: 200° C. is obtained starting from 3,4-dichloro-5-methylsulfonylbenzoic acid (melting point 215°–220° C.) by reaction with n-butylamine in an autoclave (140° C., 12 hours) to give 4-(1-butyl-amino)-3-chloro-5-methylsulfonylbenzoic acid (melting point 155°–160°

C.) and reaction with guanidine according to the procedure (see above).

EXAMPLE 13

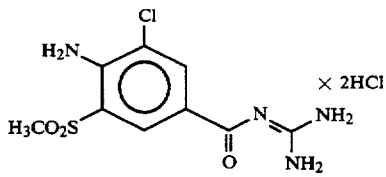

4-Amino-3-chloro-5-methylsulfonylbenzoylguanidine dihydrochloride, colorless crystals, melting point: 270° C. is obtained starting from 4-amino-3-chloro-5-methylsulfonylbenzoic acid (melting point 255°-261° C.) by reaction with guanidine according to the procedure (see above).

EXAMPLE 14

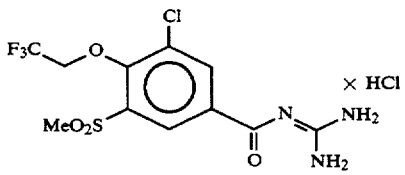

3-Chloro-4-(2,2,2-trifluoroethoxy)-5-methylsulfonylbenzoylguanidine hydrochloride, colorless crystals, melting point 261° C. is obtained starting from methyl 3,4-dichloro-5-methylsulfonylbenzoate by reaction with 2,2,2-trifluoroethanol and potassium carbonate in DMF (100° C., 6 hours) and subsequent alkaline hydrolysis to 3-chloro-4-(2,2,2-trifluoroethoxy)-5-methylsulfonylbenzoic acid (melting point 214°-220° C.) and reaction with guanidine according to the procedure (see above).

EXAMPLE 15

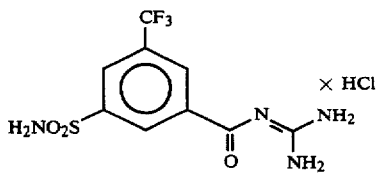

3-Sulfamoyl-5-trifluoromethylbenzoylguanidine hydrochloride, colorless crystals, melting point 235°-238° C. is obtained by reaction of 3-trifluoromethylbenzoic acid by nitration (100% strength HNO3 in 20% strength oleum, 3 hours at room temperature) to give 5-nitro-3-trifluoromethylbenzoic acid (melting point 126°-129 ° C.). Catalytic hydrogenation (platinum(IV) oxide in ethanol at room temperature, 1 atm) to 5-amino-3-trifluoromethylbenzoic acid (melting point 133°-137° C.), Meerwein reaction to give 5-chlorosulfonyl-3-trifluoromethylbenzoic acid (melting point 144°-147° C.), reaction with aqueous ammonia (25% strength, 14 hours at room temperature) to give 5-sulfamoyl-3-trifluoromethylbenzoic acid (melting point 235°-240° C.) and reaction with guanidine according to the procedure (see above).

EXAMPLE 16

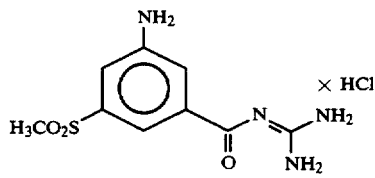

3-Amino-5-methylsulfonylbenzoylguanidine dihydrochloride, colorless crystals, melting point 264° C., is obtained by reaction of 3-methylsulfonylbenzoic acid by nitration (100% strength HNO3 in 20% strength oleum, 3 hours at room temperature) to give 5-nitro-3-methylsulfonylbenzoic acid (melting point 218°-220° C.), catalytic hydrogenation (Raney nickel in methanol at room temperature, 1 arm) to 5-amino-3-methylsulfonylbenzoic acid (melting point 300°-310° C.), and reaction with guanidine according to the procedure (see above).

EXAMPLE 17

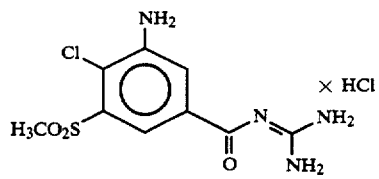

3-Amino-4-chloro-5-methylsulfonylbenzoylguanidine dihydrochloride, colorless crystals, melting point 279°-281° C., is obtained by reaction of 4-chloro-3-methylsulfonylbenzoic acid by nitration (100% strength HNO3 in 20% strength oleura, 4 hours at 90°-100° C.) to give 4-chloro-5-nitro-3-methylsulfonylbenzoic acid (melting point 190°-194° C.), reduction using sodium bisulfite (1 hour, 100° C. in water) to 5-amino-4-chloro-3-methylsulfonylbenzoic acid (melting point 265°-267° C.) and reaction with guanidine according to the procedure (see above).

EXAMPLE 18

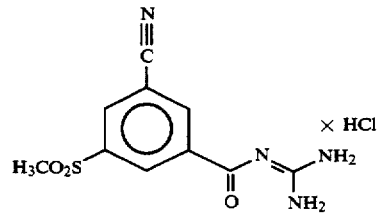

3-Cyano-5-methylsulfonylbenzoylguanidine hydrochloride, colorless to slightly yellow crystals, melting point 275°-278° C. (dec.), is obtained by Sandmeyer reaction of 3-amino-5-methylsulfonylbenzoic acid with Cu(I) cyanide to give 3-cyano-5-methylsulfonylbenzoic acid (melting point 226-228) and subsequent reaction with guanidine according to the procedure (see above).

EXAMPLE 19

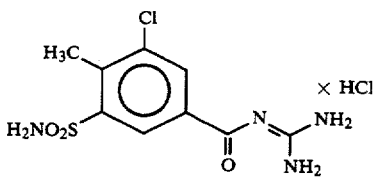

3-Chloro-4-methyl-5-sulfamoylbenzoylguanidine hydrochloride, colorless crystals, melting point 256°-259° C., is obtained from 3-chloro-4-methyl-5-sulfamoylbenzoic acid by reaction with guanidine according to the procedure (see above).

EXAMPLE 20

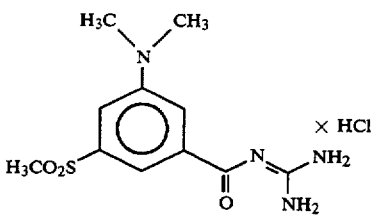

3-Dimethylamino-5-methylsulfonylbenzoylguanidine dihydrochloride, colorless crystals, melting point 278°-290° C. (dec.), is obtained by reaction of 3-amino-5-methylsulfonylbenzoic acid with methyl iodide in DMF/potassium carbonate (6 hours, 70° C.) and subsequent hydrolysis to 3-dimethyl-amino-5-methylsulfonylbenzoic acid (melting point 200°-203° C.) and subsequent reaction with guanidine according to the procedure (see above).

EXAMPLE 21

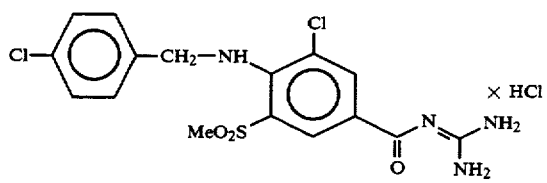

3-Chloro-4-(4 -chlorobenzylamino)-5-methylsulfonylguanidine hydrochloride is obtained according to the procedure from 3-chloro-4-(4-chlorobenzylamino)-5-methylsulfonylbenzoic acid and guanidine. Colorless crystals; melting point 209°-219° C.

EXAMPLE 22

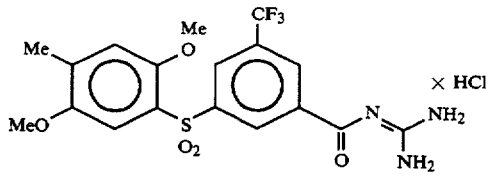

3-(2,5-Dimethoxy-4-methylphenylsulfonyl)-5-trifluoromethylbenzoylguanidine hydrochloride is obtained according to the procedure from 3-(2,5-dimethoxy-4-methylphenylsulfonyl)-5-trifluoromethylbenzoic acid and guanidine. Colorless crystals; melting point: 174° C.

EXAMPLE 23

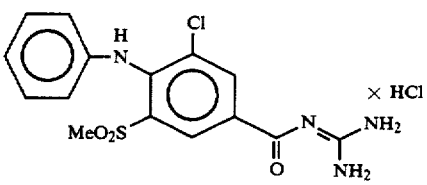

4-Anilino-3-chloro-5-methylsulfonylbenzoylguanidine hydrochloride is obtained according to the procedure from 4-anilino-3-chloro-5-methylsulfonylbenzoic acid and guanidine. Colorless crystals; melting point: 174° C. 4-Anilino-3-chloro-5-methylsulfonylbenzoic acid (melting point 187°-189° C.) is obtained by 1. heating methyl 3,4-dichloro-5-methylsulfonylbenzoate in excess aniline for 8-10 hours at 120° C. and removal of the methyl 4-anilino-3-chloro-5-methylsulfonylbenzoate (melting point 165°-169° C.) by treating the reaction mixture with 1N HCl and
2. by subsequent hydrolysis of the methyl 4-anilino-3-chloro-5-methylsulfonylbenzoate with methanolic/aqueous NaOH and treatment of the residue with 2N HCl after distilling off the solvent mixture.

We claim:

1. A benzoylguanidine of the formula I in which:

R(1) is R(4)—SO$_m$ or R(5)R(6)N—S0$_2$—, where
m is zero, 1 or 2,
R(4) and R(5) are C$_1$-C$_8$-alkyl, C$_3$-C$_6$-alkenyl or —C$_n$H$_{2n}$—R(7),
n is zero, 1, 2, 3 or 4,
R(7) is C$_5$-C$_7$-cycloalkyl or phenyl which is unsubstituted or substituted by 1-3 substituents from the group comprising
F, Cl, CF$_3$, methyl, methoxy and NR(8)R(9) where R(8) and R(9) are H or C$_1$-C$_4$-alkyl,
where R(5) also has the meaning of H, R(6) is H or C$_1$-C$_4$-alkyl,
where R(5) and R(6) together can be 4 or 5methylene groups, of which one CH$_2$ group can be replaced by O, S, NH, N—CH$_3$ or N-benzyl,
R(2) is hydrogen, F, Cl, Br, (C$_1$-C$_4$)-alkyl, O-(CH$_2$)$_m$C$_p$F$_{2p+1}$ or —X—R(10), where
m is zero or 1,
p is 1, 2 or 3,
x is O, S, or NR(11),
R(10) is H, C$_1$-C$_6$-alkyl, C$_5$-C$_7$-cycloalkyl, cyclohexylmethyl, cyclopentylmethyl, or —C$_n$H$_{2n}$—R(12) where
n is zero, 1, 2, 3 or 4 and
R(12) is phenyl which is unsubstituted or substituted by 1-3 substituents from the group comprising
F, Cl, CF$_3$, methyl, methoxy and NR(8)R(9) where R(8) and R(9) are H or C$_1$-C$_4$-alkyl,
R(11) is hydrogen or C$_1$-C$_3$-alkyl,
where R(10) and R(11) can also together be 4 or 5 methylene groups and a CH$_2$ group can be replaced by O, S, NH, N—CH$_3$ or N-benzyl,
R(3) is defined as R(1), or is C$_1$-C$_6$-alkyl, nitro, cyano, trifluoromethyl, F, Cl, Br, I or —X—R(10) where X is O, S or NR(11)

R(10) is H, $C_1$-$C_6$-alkyl, $C_5$-$C_7$-cycloalkyl, cyclohexylmethyl, cyclopentylmethyl or —$C_nH_{2n}$—R(12) where n is from zero to 4 and R(12) is phenyl which is unsubstituted or substituted by 1–3 substituents from the group comprising F, Cl, $CF_3$, methyl, methoxy and NR(8)R(9) where R(8) and R(9) are H or $C_1$-$C_4$-alkyl, R(11) is H or $C_1$-$C_3$-alkyl, where R(10) and R(11) can also together be 4 or 5 methylene groups and a $CH_2$ group can be replaced by O, S, NH, N—$CH_3$ or N-benzyl, and their pharmaceutically tolerable salts, but where compounds are excluded in which, at the same time: R(1) is R(4)—$SO_m$ where m=zero to 2 or R(5)R(6) $NSO_2$—, R(2) is halogen, ($C_1$-$C_4$)-alkyl, and R(3) is —NR(10)R(11).

2. A compound I as claimed in claim 1, wherein:

R(1) is R(4)—$SO_m$ or R(5)R(6)N—$O_2$—, where m is zero, 1 or 2,

R(4) is methyl or —$C_nH_{2n}$—R(7), n is zero or 1,

R(7) is phenyl which is unsubstituted or substituted by 1–3 substituents from the group comprising Cl, $CF_3$, methyl and methoxy, R(5) is H, $C_1$-$C_6$-alkyl, allyl or —$C_nH_{2n}$—R(7), n is zero or 1, 2 or 3

R(7) is phenyl which is unsubstituted or substituted by 1–3 substituents from the group comprising F, Cl, $CF_3$, methyl, methoxy and NR(8)R(9) where R(8) and R(9) are H or methyl, R(6) is H or methyl, where R(5) and R(6) can together be 4 or 5 methylene groups, of which one $CH_2$ group can be replaced by an O, S, N—$CH_3$ or N-benzyl, R(2) is hydrogen, O—$CH_2CF_3$ or —X—R(10), where X is O, S or NR(11), R(10) is H, $C_1$-$C_6$-alkyl or —$C_nH_{2n}$—R(12) where n for X having the meaning of oxygen or sulfur is zero, and for X having the meaning of NR(12) is zero or 1, and R(12) is phenyl which is unsubstituted or substituted by 1–3 substituents from the group comprising F, Cl, $CF_3$ and methyl, R(11) is hydrogen or ($C_1$-$C_3$)-alkyl, where R(10) and R(11) can also together be 4 or 5 methylene groups and a $CH_2$ group can be replaced by O, S, N—$CH_3$ or N-benzyl, R(3) is methyl, nitro, cyano, trifluoromethyl, F, Cl or —X—R(10) where X is O, S or NR(11), R(10) is H, $C_1$-$C_6$-alkyl or —$C_n$—$H_{2n}$—R(12) where n is zero or 1, R(12) is phenyl which is unsubstituted or substituted by 1–3 substituents from the group comprising Cl, $CF_3$, methyl and methoxy, R(11) is hydrogen or ($C_1$-$C_3$)-alkyl where R(10) and R(11) can also together be 4 or 5 methylene groups, and their pharmaceutically tolerable salts.

3. A compound I as claimed in claim 1, wherein:

R(1) is R(4)—$SO_2$— or R(5)R(6)N—$SO_2$— where R(4) is methyl,

R(5) and R(6) are hydrogen,

R(2) is hydrogen, —O—$CH_2$—$CF_3$ or X—R(10) where

X is oxygen or N—R(11),

R(10) is H, $C_1$-$C_6$-alkyl or —$C_nH_{2n}$—R(12) where n=zero or 1

R(12) is phenyl which is unsubstituted or substituted by a substituent from the group comprising F, Cl and methyl, R(11) is hydrogen or $C_1$-$C_3$-alkyl, R(3) is methyl, F or Cl, and their pharmacologically tolerable salts.

4. A compound I as claimed in claim 1, selected from the group comprising 3-chloro-4-N,N-diethylamino-5-methylsulfonylbenzoylguanidine hydrochloride and 3,4-dimethyl-5-sulfamoylbenzoylguanidine hydrochloride.

5. A pharmaceutical composition comprising an effective amount for use as a pharmaceutical of a benzoylguanidine of the formula I as set forth in claim 1 together with a pharmaceutically acceptable carrier.

6. A method for the treatment of arrhythmias or angina pectoris which comprises administering to a mammal in need of such treatment a pharmaceutical composition as set forth in claim 5.

7. A method for the treatment of arrhythmias or angina pectoris which comprises administering to a mammal in need of such treatment an effective amount of a benzoylguanidine of the formula I as set forth in claim 1.

* * * * *

UNITED STATES PATENT AND TRADEMARK OFFICE
CERTIFICATE OF CORRECTION

PATENT NO. : 5,373,024

DATED : December 13, 1994

INVENTOR(S) : Florian LANG et al.

It is certified that error appears in the above-indentified patent and that said Letters Patent is hereby corrected as shown below:

Title page : line 3 change "of" to --or--.

Claim 1, column 14, beneath line 31 supply missing formula I

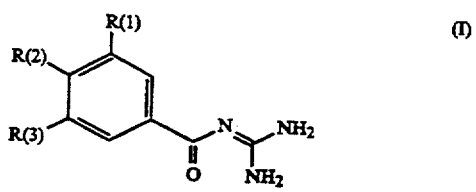

UNITED STATES PATENT AND TRADEMARK OFFICE
CERTIFICATE OF CORRECTION

PATENT NO. : 5,373,024
DATED : December 13, 1994
INVENTOR(S) : Florian LANG et al.

It is certified that error appears in the above-indentified patent and that said Letters Patent is hereby corrected as shown below:

Claim 1, column 14, line 46 change "5methylene" to --5 methylene--.

Claim 2, column 15, line 23 change "$O_2$" to --$SO_2$--.

Claim 2, column 15, line 30 change "$C_1-C_6$" to --$C_1-C_6$--.

Claim 2, column 15, line 31 change "or" to --or--.

Signed and Sealed this

Thirteenth Day of June, 1995

Attest:

BRUCE LEHMAN

Attesting Officer    Commissioner of Patents and Trademarks